US009161752B2

(12) United States Patent
Esaki

(10) Patent No.: US 9,161,752 B2
(45) Date of Patent: Oct. 20, 2015

(54) RHENIUM TUNGSTEN WIRE, METHOD OF MANUFACTURING THE WIRE AND MEDICAL NEEDLE USING THE WIRE

(75) Inventor: Motoaki Esaki, Yokosuka (JP)

(73) Assignees: KABUSHIKI KAISHA TOSHIBA, Tokyo (JP); TOSHIBA MATERIALS CO., LTD., Yokohama-Shi (JP)

( * ) Notice: Subject to any disclaimer, the term of this patent is extended or adjusted under 35 U.S.C. 154(b) by 909 days.

(21) Appl. No.: 13/254,044

(22) PCT Filed: Dec. 25, 2009

(86) PCT No.: PCT/JP2009/071624

§ 371 (c)(1), (2), (4) Date: Aug. 31, 2011

(87) PCT Pub. No.: WO2010/100808

PCT Pub. Date: Sep. 10, 2010

(65) Prior Publication Data

US 2011/0319931 A1 Dec. 29, 2011

(30) Foreign Application Priority Data

Mar. 2, 2009 (JP) ................................ 2009-048319

(51) Int. Cl.
*C22C 27/04* (2006.01)
*A61B 17/06* (2006.01)
(Continued)

(52) U.S. Cl.
CPC ................. *A61B 17/06* (2013.01); *B22F 5/003* (2013.01); *B22F 5/12* (2013.01); *C22C 1/045* (2013.01);
(Continued)

(58) Field of Classification Search
CPC ................ B22F 3/02; B22F 3/12; B22F 3/24; C22C 27/04
USPC ........................................................ 420/432
See application file for complete search history.

(56) References Cited

U.S. PATENT DOCUMENTS 5,415,707 A 5/1995 Bendel et al.
8,062,437 B2 * 11/2011 Cichocki et al. ............. 148/567
(Continued)

FOREIGN PATENT DOCUMENTS

EP 1 435 398 A1 7/2004
JP 59 59867 4/1984
(Continued)

OTHER PUBLICATIONS

International Preliminary Report on Patentability issued Sep. 13, 2011 in PCT/JP09/071624 filed Dec. 25, 2009.
(Continued)

*Primary Examiner* — Jie Yang

(74) *Attorney, Agent, or Firm* — Oblon, McClelland, Maier & Neustadt, L.L.P.

(57) ABSTRACT

The present invention provides a rhenium tungsten wire comprising 10 to 30 mass % of rhenium and balance of tungsten, and having a wire diameter D of 0.10-0.40 mm, wherein a tensile strength T (N/mm$^2$) of the rhenium tungsten wire exists within a range specified by an equation (1).

$$6314.6\times D^2-7869.3\times D+4516.3\leq T\leq 5047.4\times D^2-7206.4\times D+5129.2 \quad (1).$$

In a case where the medical needle is manufactured from the above rhenium tungsten wire, crack and breakage hardly occur at a time of performing a pressing work or a bending work, so that a production yield and durability of the resultant products can be greatly improved.

13 Claims, 2 Drawing Sheets

(51) Int. Cl.

| | |
|---|---|
| ***B22F 5/00*** | (2006.01) |
| ***B22F 5/12*** | (2006.01) |
| ***C22C 1/04*** | (2006.01) |
| ***C22F 1/00*** | (2006.01) |
| ***C22F 1/18*** | (2006.01) |
| *A61B 17/00* | (2006.01) |
| *B22F 3/24* | (2006.01) |

(52) U.S. Cl.
CPC . *C22C 27/04* (2013.01); *C22F 1/00* (2013.01); *C22F 1/18* (2013.01); *A61B 2017/00526* (2013.01); *A61B 2017/00831* (2013.01); *B22F 2003/248* (2013.01); *B22F 2998/10* (2013.01)

(56) References Cited

U.S. PATENT DOCUMENTS

| | | | |
|---|---|---|---|
| 2004/0244879 | A1 | 12/2004 | Tanaka et al. |
| 2008/0295927 | A1 | 12/2008 | Cichocki et al. |
| 2008/0300552 | A1 | 12/2008 | Cichocki et al. |

FOREIGN PATENT DOCUMENTS

| | | |
|---|---|---|
| JP | 3 219039 | 9/1991 |
| JP | 7 204207 | 8/1995 |
| JP | 2002 75059 | 3/2002 |
| JP | 2002 356732 | 12/2002 |
| WO | 03 031668 | 4/2003 |

OTHER PUBLICATIONS

International Search Report issued Mar. 23, 2010 in PCT/JP09/071624 filed Dec. 25, 2009.

Combined Chinese Office Action and Search Report issued Apr. 14, 2014 in Patent Application No. 200980157825.1 (with English language translation).

Office Action issued Jan. 20, 2015, in corresponding Japanese Patent Application No. 2014-028428.

* cited by examiner

RHENIUM TUNGSTEN WIRE, METHOD OF MANUFACTURING THE WIRE AND MEDICAL NEEDLE USING THE WIRE

This application is a 371 of PCT/JP2009/071624, filed Dec. 25,2009. Priority to Japanese patent application 2009-048319, filed Mar. 2,2009, is claimed.

TECHNICAL FIELD

The present invention relates to a rhenium tungsten wire, a method of manufacturing the rhenium tungsten wire and a medical needle using the rhenium tungsten wire, and particularly relates to a rhenium tungsten wire, a method of manufacturing the rhenium tungsten wire and a medical needle formed by using the rhenium tungsten wire having a high strength and causing less crack formation or breakage even if the rhenium tungsten wire is worked into the medical needle, and capable of manufacturing the medical needle or the like having a good usability with a high production yield.

BACKGROUND ART

Conventionally, a needle made of stainless steel has been generally used as a sewing needle for medical use. In recent years, for the purpose of lightening a patient's load, a need for a thinner medical needle has been increased and demanded. However, when the needle is made to be thinner, deflection and bending of the needles are liable to occur, so that there has been posed a problem such that an operability of the needle is disadvantageously lowered in a short time period.

In order to prevent the above problem, a raw material having higher strength and rigidity than those of the stainless steel has been demanded. Particularly, a rhenium tungsten alloy (Re—W alloy) is a material having high strength and rigidity due to a solution-strengthening function of tungsten into rhenium. Concretely, in a case where a wire diameter D (mm) is within a range of 0.10 to 0.40 mm and a tensile strength of the rhenium tungsten alloy wire is expressed to be T ($N/mm^2$), a maximum value of T ($N/mm^2$) was within a range indicated by an equation (3) hereunder, which is expressed as a function of the wire diameter D (mm).

$$T<6314.6\times D^2-7869.3\times D+4516.3 \quad (3)$$

On the other hand, for example, Japanese Patent Laid-Open (Unexamined) No. 7-204207 (Patent Literature 1) discloses a medical needle for surgical use. The medical needle is made of tungsten alloy containing rhenium (Re) at an amount of 30 mass % or less. The Patent Literature 1 reported that medical needle for surgical use, having high tensile elastic modulus and high yield strength in tension, can be obtained.

CITATION LIST

Patent Literature

Patent Document 1: Japanese Patent Application (Laid-Open) No. 7-204207

However, the conventional rhenium tungsten wire constituting the medical needle disclosed in the above prior art literature takes a maximum value of the tensile strength within the range indicated by the equation (3). Further, the rhenium tungsten wire having a tensile strength exceeding a value calculated by the equation (3) has not been obtained yet, so that a sufficient performance could not been obtained.

Further, in the medical needle disclosed in the Patent Literature 1, crack is liable to be formed at a time of manufacturing the rhenium tungsten wire, and the crack and breakage are liable to occur at a time of performing a pressing work or a bending work for preparing a bended sewing needle from the rhenium tungsten wire. As a result, there has been posed a problem such that a production yield of the resultant products is greatly lowered.

In this connection, as a method of preventing the above crack formation and the breakage at a bended portion, there has been generally adopted a method in which the rhenium tungsten wire is subjected to an annealing treatment. However, even if the annealing treatment is conducted to the medical needle described in the Patent Literature 1, there may be posed a fatal problem such that the strength of the medical needle would rather lowered and a sufficient strength cannot be obtained.

DISCLOSURE OF INVENTION

The present invention had been accomplished in view of the above circumstances and problems. An object of the present invention is to provide a rhenium tungsten wire, a method of manufacturing the rhenium tungsten wire and a medical needle formed by using the rhenium tungsten wire in which the tensile strength is improved to be 1.2-1.4 times higher than those of conventional rhenium tungsten wires, usability of the medical needle can be improved, a crack is hardly occur when the rhenium tungsten wire is subjected to the pressing work or the bending work, and a breakage hardly occur to a bended portion.

In order to solve the aforementioned problems, the present invention provides a rhenium tungsten wire comprising 10 to 30 mass % of rhenium and balance of tungsten, and having a wire diameter D of 0.10-0.40 mm, wherein a tensile strength T ($N/mm^2$) of the rhenium tungsten wire exists within a range specified by an equation (1).

$$6314.6\times D^2-7869.3\times D+4516.3\leq T\leq 5047.4\times D^2-7206.4\times D+5129.2 \quad (1)$$

In another aspect of the present, in order to solve the aforementioned problems, the present invention provides a method of manufacturing the rhenium tungsten wire, the method comprises: a mixing step for mixing 70-90 mass % of tungsten powder having an average grain size D50 of 25 μm or less and an average grain size D90 of 60 μm or less with 10-30 mass % of rhenium powder having an average grain size D50 of 45 μm or less thereby to prepare a material powder mixture; a molding step for molding thus obtained material powder mixture thereby to form a molded body; a sintering step for sintering the molded body thereby to prepare a sintered body; a rolling step for rolling thus obtained sintered body; a swaging step for swaging and working the rolled sintered body; a recrystallizing step for recrystallizing the swaged sintered body; another swaging and working step for further swaging and working the recrystallized sintered body; a drawing and working step for drawing and working the swaged sintered body thereby to prepare a wire member; and an electrolytic polishing step for electrolytically polishing a surface of the wire member.

According to the rhenium tungsten wire and the method of manufacturing the rhenium tungsten wire of the present invention, a tensile strength of the wire member can be improved to be 1.2-1.4 times higher than those of conventional wire members. In a case where a medical needle is formed by working this wire member, an usability of the medical needle can be improved, and there can be obtained the rhenium tungsten wire which hardly occurs crack or breakage when the wire member is subjected to the pressing work or the bending work. As a result, when using the wire member, there can be provided a medical needle having an excellent usability.

EMBODIMENTS FOR CARRYING OUT THE INVENTION

Figure 1:
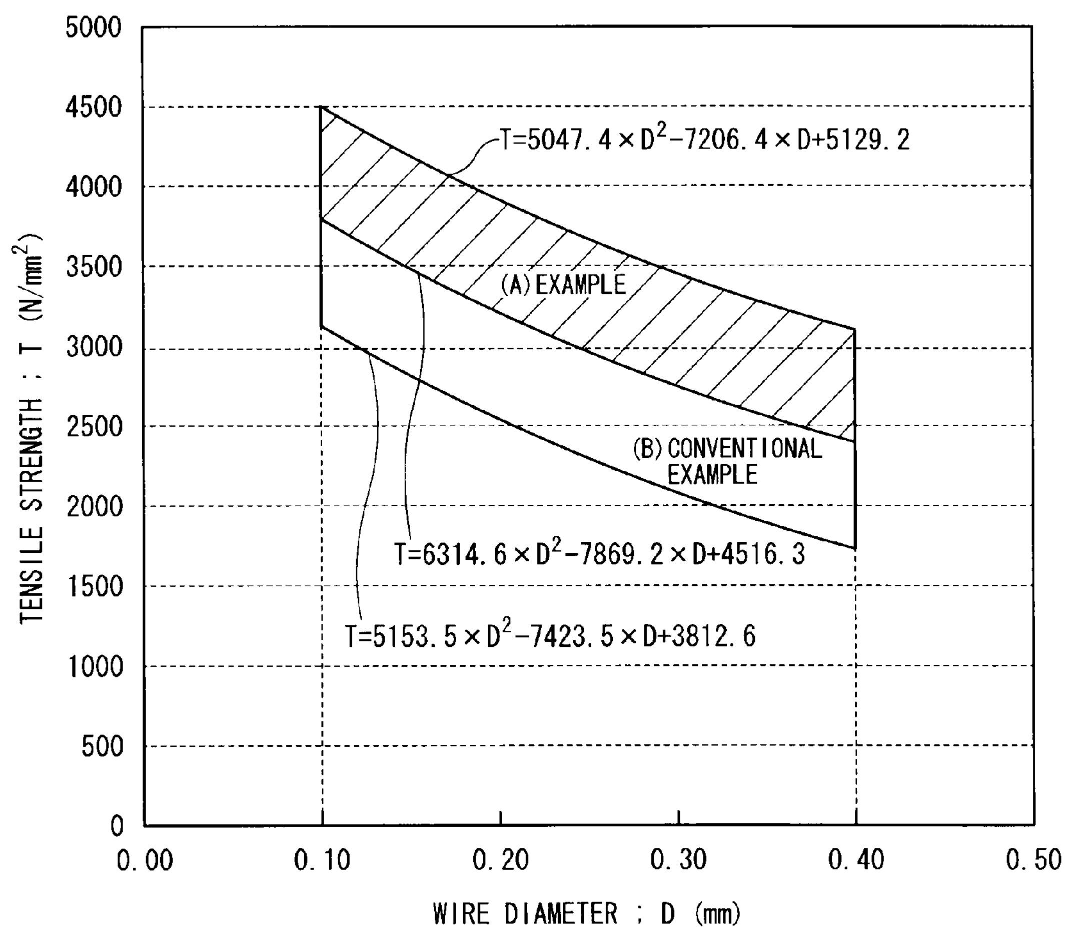
FIG. 1 is a graph showing a relation between the wire diameter and the tensile strength of the rhenium tungsten wires of Examples according to the present invention and Comparative Examples.

Hereinafter, the embodiment for carrying out the present invention will be explained in more detail.

An embodiment of the present invention provides a rhenium tungsten wire comprising 10 to 30 mass % of rhenium and balance of tungsten, and having a wire diameter D of 0.10-0.40 mm, wherein a tensile strength T ($N/mm^2$) of the rhenium tungsten wire exists within a range specified by the following equation (1) which is a relation formula.

$$6314.6\times D^2-7869.3\times D+4516.3\leq T\leq 5047.4\times D^2-7206.4\times D+5129.2 \quad (1)$$

Notes, the wire diameter D satisfies a relation: $0.10\ mm\leq D\leq 0.40\ mm$.

Concretely, when the wire diameter D is 0.10 mm, the tensile strength T is 3792.5 to 4459.0 ($N/mm^2$), while when the wire diameter D is 0.40 mm, the tensile strength T is 2378.9 to 3054.2 ($N/mm^2$). Namely, the values of the wire diameter D and the tensile strength T of the rhenium tungsten wire according to the present embodiment exists within a range specified by a region (A) indicated in FIG. 1.

In the rhenium tungsten wire (Re—W wire member) of this embodiment according to the present invention, a rhenium content is specified to be 10 to 30 mass %. However, 24 to 27 mass % is more preferable. Further, the Re—W wire member may contain various impurities that are originated from a raw material and process steps.

When the rhenium content is within the above range, it becomes possible to suppress the generation of crack or breaking of wire at the time of performing a plastic work or the drawing work. Namely, when the rhenium content is less than 10 mass %, the crack is liable to generate at a portion along a fiber structure which is formed when the wire member is subjected to the drawing work. In contrast, when the rhenium content exceeds 30 mass %, a hard a phase is generated at a portion where an excessive amount of rhenium exists in the fiber structure, thus becoming a cause of crack and breaking of the wire at a time of the drawing work.

Further, when the tensile strength T ($N/mm^2$) of the rhenium tungsten wire (Re—W wire member) of this embodiment according to the present invention is less than a value calculated by a relation formula: $6314.6\times D^2-7869.3\times D+4516.3$, a structural strength of the rhenium tungsten wire is insufficient, so that required characteristics for the medical needle or the like cannot be satisfied.

On the other hand, in a case where the tensile strength T exceeds a value ($5047.4\times D^2-7206.4\times D+5129.2$), a hardness of the wire member becomes to be excessively high, a deformation resistance of the wire member in the drawing and working step becomes large, so that the wire breaking during the working, a surface defect, and a scattering in wire diameter are easily generated. Furthermore, a wear (abrasion) and crack of drawing dice are increased, and a load with respect to a wire manufacturing facility becomes to be excessive, so that it becomes difficult to secure a stable quality of the rhenium tungsten wire, thus being not preferable.

The rhenium tungsten wire of this embodiment according to the present invention may contain Fe, Mo, Si, Mg, Al and Ca as impurities at a total content (amount) of 200 ppm or less. The total content of 100 ppm or less is more preferable, and 70 ppm or less is furthermore preferable. These elements as unavoidable impurities are contained in the wire by influences of the raw material and the manufacturing processes. However, when the total content of the impurities is controlled to be within the above range, a bending property of the rhenium tungsten wire is improved, so that the bending work and the pressing work for the wire member can be easily performed.

The method of manufacturing the rhenium tungsten wire according to the present invention comprises:

a mixing step for mixing 70-90 mass % of tungsten powder having an average grain size D50 of 25 μm or less and an average grain size D90 of 60 μm or less with 10-30 mass % of rhenium powder having an average grain size D50 of 45 μm or less thereby to prepare a material powder mixture;.

a molding step for molding thus obtained material powder mixture thereby to form a molded body;

a sintering step for sintering the molded body thereby to prepare a sintered body;

a rolling step for rolling thus obtained sintered body;

a swaging step for swaging and working the rolled sintered body;

a recrystallizing step for recrystallizing the swaged sintered body;

another swaging and working step for further swaging and working the recrystallized sintered body;

a drawing and working step for drawing and working the swaged sintered body thereby to prepare a wire member; and an electrolytic polishing step for electrolytically polishing a surface of the wire member.

The manufacturing process of the rhenium tungsten wire of the embodiment according to the present invention comprises: for example, a mixing step for mixing the tungsten powder having a predetermined grain size with the rhenium powder as material powders having a predetermined grain size thereby to prepare a material powder mixture;.

a molding step for molding thus obtained material powder mixture thereby to form a molded body;

a calcining step for calcining the molded body thereby to prepare a calcined body;

a main-sintering step for main-sintering the calcined body thereby to prepare a sintered body;

a first swaging step for swaging the sintered body;

an annealing step for conducting a heat treatment (annealing) to the swaged sintered body;

a rolling step for rolling thus obtained annealed sintered body;

a second swaging and working step for swaging and working the rolled sintered a recrystallizing step for recrystallizing the swaged sintered body;

another swaging and working step for further swaging and working the recrystallized sintered body;

a third swaging step for further swaging and working the recrystallized sintered body.

a drawing step for drawing and working the swaged sintered body thereby to prepare a wire member; and an electrolytic polishing step for electrolytically polishing a surface of the wire member.

The mixing step of the material powders for forming the rhenium tungsten wire of the embodiment according to the present invention is characterized in that 70-90 mass % of tungsten powder having an average grain size D50 of 25 μm or less and an average grain size D90 of 60 μm or less is mixed with 10-30 mass % of rhenium powder having an average grain size D50 of 45 μm or less.

When the average grain size D50 of the tungsten powder is specified to be 25 μm or less and an average grain size D90 of the tungsten powder is specified to be 60 μm or less, a uniform mixing of the tungsten powder and the rhenium powder is sufficiently advanced, so that it becomes possible to mitigate a scattering of rhenium concentration in the rhenium-tungsten wire.

The average grain size D50 of the tungsten powder is more preferably set to a range of 10 μm to 20 μm, and the average grain size D90 is more preferably set to 50 μm or less. In a case where the average grain size D50 of the tungsten powder exceeds 25 μm or the average grain size D90 exceeds 60 μm, a dispersion state of rhenium becomes to be non-uniform and a diffusion state is deteriorated, so that a wire member having a uniform strength cannot be obtained.

On the other hand, when the average grain size D50 of the rhenium powder is set to 45 μm or less, a ductility of the rhenium tungsten wire is increased. Therefore, even in a case where the pressing work or the bending work is performed for preparing a secondary product such as medical needle or the like from the rhenium tungsten wire, it becomes possible to effectively reduce the crack or breakage (breaking) to be generated in the rhenium tungsten wire.

The average grain size D50 of the rhenium powder is more preferably set to a range of 10 μm to 20 μm. In this connection, when the average grain size D50 of the rhenium powder exceeds 45 μm, the ductility of the rhenium tungsten wire is lowered. As a result, when the pressing work or the bending work is performed for manufacturing the secondary product, there may be posed a fear that the crack or the breakage will be generated in the rhenium tungsten wire.

By the way, a content of impurities except rhenium contained in the tungsten powder is preferably set to 200 ppm or less, more preferably set to 100 ppm or less. When the above impurity content exceeds 200 ppm, the ductility of the rhenium tungsten wire is lowered. Therefore, when the pressing work or the bending work is performed for manufacturing the secondary product from the rhenium tungsten wire, there may be also posed a fear that the crack or the breakage will be generated in the rhenium tungsten wire.

As the impurity content contained in the tungsten powder, when iron (Fe) content is less than 50 ppm, molybdenum (Mo) content is less than 30 ppm, oxygen (O) content is less than 0.2 wt. % and potassium (K) content is less than 5 ppm, the ductility of the rhenium tungsten wire is increased. Therefore, even in a case where the pressing work or the bending work is performed for manufacturing the secondary product from the rhenium tungsten wire, it becomes possible to effectively reduce the crack or breakage (breaking) to be generated in the rhenium tungsten wire.

Further, in the above molding process (step) for molding the material powder mixture of the tungsten powder and the rhenium powder each having a predetermined average grain size, a pressing force is applied to the material powder mixture prepared in the mixing step by utilizing a die-press-molding machine or the like, thereby to obtain a rod-shaped molded body. In this molding step, it is preferable to perform a press-densifying operation so that a relative density of the molded body is controlled to be within a range of 45 to 50%.

Next, with respect to the molded body obtained in the molding step, a calcining step (provisionally sintering step) may be performed in advance so as to make it easy to handle the molded body at a main sintering step which is a post-process of the molding step. The calcining step is a process in which the molded body is heated and passed through a continuous hydrogen furnace of which temperature is controlled to be 1300 to 1400° C. The passing through the furnace and a heating operation is performed, for example, under a condition that a feed speed of the molded body is set to 4.5 to 5.0 cm/min (heating time is 20 min. to 1 hour).

Subsequently, with respect to the calcined body (provisionally sintered body), a main sintering step for obtaining an actual sintered body is performed by utilizing, for example, a current-carrying sintering method (electrically heating and sintering method). In the current-carrying sintering step, the calcined body is subjected to the current-carrying sintering operation in a bell jar through which hydrogen gas or the like flows. As sintering conditions in the current-carrying sintering operation, it is preferable that a sintering temperature is set to within a range of 2800 to 3100° C., and a sintering time shall be set to 60 to 90 min. In this case, a sintering current shall be set to 3700 to 4000 A. In a case where the sintering current is less than 3700 A, the sintering temperature is low, so that rhenium would not diffuse whereby a uniform solution state cannot be obtained, thus being not preferable.

After completion of the above main sintering step, it is preferable that the actual sintered body has a relative density of 95% or more, more preferably, 98% or more. For example, in case of the rhenium content of 26 mass %, a density of the sintered body is preferably 19.1 to 19.6 g/cm$^3$ which corresponds to a relative density of 96.86 to 99.39%. In a case where the relative density of the actual sintered body is within the above range, it becomes possible to reduce crack, chipping or breakage to be generated in a swaging step which is a post-step for the main sintering step.

With respect to the rhenium tungsten sintered body (ingot) obtained in the main sintering step, a first swaging and working treatment is performed thereby to obtain a rod-shaped rhenium tungsten member. It is preferable that the first swaging and working treatment is performed under a heated state at a temperature of 1300 to 1500° C.

Then, with respect to the rhenium tungsten member obtained in the swaging and working step, an annealing step is performed. The annealing step can be performed in accordance with, for example, a current-carrying anneal treatment in which the rhenium tungsten member is treated in a hydrogen atmosphere at a temperature of 1500 to 1600° C., and the treating time is 1 to 5 min. A current at this current-carrying treatment is, for example, 2700 to 3100 A.

Thereafter, with respect to the rhenium tungsten member obtained in the annealing step, a rolling step is performed. It is preferable that the rolling step is performed under a heated condition at a temperature of 1350 to 1550° C. Next, with respect to the rhenium tungsten member subjected to the rolling step, a second swaging step is performed. It is preferable that the second swaging step is performed under a heated state at a temperature of 1300 to 1500° C.

Then, with respect to the rhenium tungsten member subjected to the second swaging step, a recrystallizing treatment is performed by conducting a predetermined heat treatment. This recrystallizing treatment can be performed by conducting a high frequency induction heating using, for example, a high frequency induction heating device. A treating temperature is 2300 to 2600° C., and more preferable temperature range is 2400 to 2500° C.

The recrystallizing treatment is performed until a crystal grain size at a specified cross section falls within a range of 10 to 100 μm. The above cross section is obtained by cutting the rhenium tungsten member in a direction perpendicular to a longitudinal direction of the rhenium tungsten member.

A magnitude (size) of the crystal grain is preferably set to 10 to 50 μm, more preferably 20 to 50 μm. When the crystal grain size of the rhenium tungsten member is within the above range, it becomes possible to suitably maintain a tensile strength of the rhenium tungsten member. In addition, a micro crack is hardly occur in a structure of the rhenium tungsten member, so that it is possible to suppress the breaking or the crack formation in the rhenium tungsten member at a time of pressing work of the product or a bending work of the member.

On the other hand, when the crystal grain size is less than 10 μm, it becomes difficult to conduct a drawing work (step) to be performed to the wire member after completion of the recrystallizing treatment, thus being not preferable.

In order to control the crystal grain size of the rhenium tungsten wire after completion of the recrystallizing treatment so that the crystal grain size falls within a preferable range, it is preferable that the wire diameter at which the recrystallizing treatment is performed is 4 to 8 mm, more preferably 5 to 7 mm. In a case where the recrystallizing treatment is performed when the wire diameter is less than 4 mm, a residual stress caused in crystals is large, so that the crystal grain size is coarsened whereby the strength of the wire member is disadvantageously lowered, thus being not preferable.

On the other hand, in a case where the recrystallizing treatment is performed at a state where the wire diameter of the wire member exceeds 8 mm, many working steps are required in order to control the wire diameter to 0.10 to 0.40 mm which is aimed by the present invention, thus being not preferable in view of a manufacturing efficiency.

Then, with respect to the rhenium tungsten member subjected to the recrystallizing treatment (recrystallizing step), a third swaging step is performed, thereafter a drawing and working step is performed. In this connection, it is preferable that a total reduction rate Rd (%) in working steps including this third swaging step and the drawing step is within a range expressed by the following equation (2):

$$Rd \geq (-0.04 \times D^2 + 2 \times 10^{-1\ 3} \times D + 1) \times 100\% \quad (2)$$

wherein D satisfies a relation formula: 0.10 mm≤D≤0.40 mm, Rd denotes the total reduction rate (%), and D denotes a diameter (mm) of the wire member.

For example, when D is 0.10 mm, the total reduction rate Rd is preferably set to 99.96% or more. In contrast, when D is 0.40 mm, the total reduction rate Rd is preferably set to 99.36% or more. It is also preferable that this third swaging step is performed under a heated state of which temperature is 1300 to 1500° C., and a reduction rate per one pass is controlled to be 12 to 18%.

Then, with respect to the rhenium tungsten member subjected to the third swaging step, a drawing and working step is performed. It is preferable that this drawing and working step is performed until the total reduction rate becomes 95% or more. The total reduction rate means a ratio of a cross sectional area of the rhenium tungsten member after the drawing step with respect to a cross sectional area of the rhenium tungsten member before starting the drawing step. Further, this total reduction rate is preferably set to 97% or more.

In this connection, a reduction ratio indicates a ratio of decreasing cross sectional area of a raw material between before and after the working step. For example, when a cross sectional area of the raw material before the drawing and working step is 100 while the cross sectional area after the drawing and working step is 25, the reduction ratio is calculated to be 75%. The total reduction ratio indicates a ratio of decreasing cross sectional area of a raw material between before and after all the drawing and working steps.

In the drawing and working step, a reduction rate per one-pass of working is controlled depending on a degree of the total reduction rate. At a stage where the total reduction rate in the swaging step is 0% or more and less than 86%, a reduction rate per one-pass of working is controlled to be 28% to 37%. On the other hand, at a stage where the total reduction rate in the drawing step to be performed after the swaging step is 86% or more and less than 97%, a reduction rate per one-pass of working is controlled to be 20% to 30%. Further, at a stage of the total reduction rate of 97% or more, a reduction rate per one-pass of working is controlled to be 17% to 25%. The drawing step is preferably performed under a heated condition with a temperature range of 800° C. to 1100° C.

Thereafter, with respect to the rhenium tungsten wire subjected to a strainer work after the drawing step, an electrolytic polishing work is performed for the purpose of removing a lubricant agent adhered to a surface of the wire at the drawing step or removing an oxide layer formed to the surface of the wire. This electrolytic polishing work is performed, for example, by electro-chemically polishing the surface of a metal wire member in an aqueous solution of sodium hydrate with a concentration of 7 to 15 mass %.

The rhenium tungsten wire of Embodiment according to the present invention can improve a tensile strength of the wire to be 1.2-1.4 times higher than those of conventional wires. In addition, it becomes possible to greatly reduce cracks and breakings to be generated at the pressing work or the bending work the wire. Therefore, it becomes also possible to perform a work of bending the wire so as to provide a curbed shape with a high production yield, so that the wire can be preferably used to a secondary fabricating product such as medical needle or the like which is worked into a curbed shape.

Figure 2:
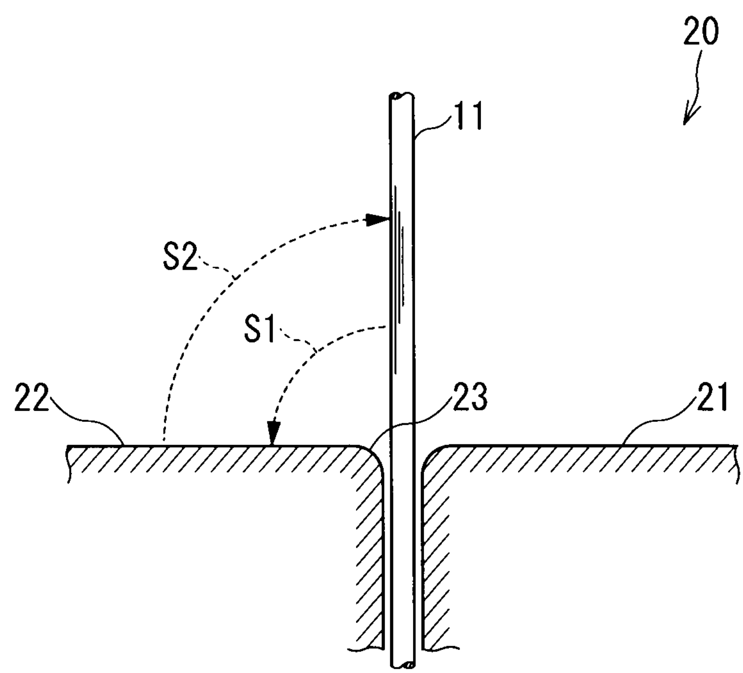
FIG. 2 is a cross sectional view illustrating a bending test method and a testing apparatus for evaluating the rhenium tungsten wires of Examples according to the present invention and Comparative Examples.

A bending property of thus manufactured rhenium tungsten wire as described above can be evaluated by using a bending test apparatus 20 shown in FIG. 2. This bending test apparatus 20 is configured by comprising: a pair of a first chucking member 21 and a second chucking member 22 for clamping the rhenium tungsten wire 11.

A concrete evaluation method is as follows. Namely, the evaluation method comprises: a first step S1 in which a rhenium tungsten wire 11 having a diameter of 0.10 to 0.40 mm is clamped and fixed by the first chucking member 21 and the second chucking member 22, and the chucked straight rhenium tungsten wire 11 is bended at a bending angle of almost 90 degree along a curbed surface portion 23 having a curvature radius of 0.3 mm; and a second step S2 in which the bended state of the wire is returned to the above straight state. The above first step S1 and the second step S2 are alternately repeated. One reciprocation comprising the first step S1 and the second step S2 is counted as one bending time. The evaluation is performed by counting a total bending times until the rhenium tungsten wire 11 causes a crack or breaking.

When the rhenium tungsten wire thus prepared through the above processes (steps) is subjected to the strainer work, a cutting work and a cutting-edge work, a medical needle can be manufactured. Further, there may be a case where a pressing work or a fusion work is added in addition to the above processes.

When the rhenium tungsten wire of this embodiment according to the present invention is cut and worked, the worked wire can be used as the medical needle. The rhenium tungsten wire according to the present invention has a high tensile strength and a good bending property, the rhenium tungsten wire is preferably used as the medical needle.

A cross sectional shape is formed to provide not only a circular shape, but also an elliptical shape, a triangular shape, a trapezoidal shape, a rectangular shape, a hexagonal shape, or the like so as to meet the respective usages. A top end may be worked to provide a thin shape, a round shape, a shape provided with a sharp portion formed by means of a cutting edge. The shape is selected in accordance with the various usages.

A shape of the needle is selected to provide a straight shape or a bended shape or the like in accordance with the various usages. However, in general, the bended shape is preferably adopted. Concretely, a needle portion (top end portion) has a length ratio of about ¼ to ¾ with respect to a circumferential length (total length). Furthermore, the needle may be also configured to comprise a means for engaging a sewing thread at a side opposing to the top end of the needle.

Next, Examples of the present invention will be explained hereunder. However, the present invention shall not be limitedly interpreted thereto.

EXAMPLE 1

74 parts by weight of tungsten powder having an average grain size D50 of 20 μm and an average grain size D90 of 50 μm was mixed with 26 parts by weight of rhenium powder having the average grain size D50 of 20 μm by means of a ball mill thereby to prepare a material powder mixture. Impurity contents of the tungsten powder are as follows. Namely, a content of Fe was less than 50 ppm, Mo was less than 20 ppm, O was less than 0.1 wt %, K was less than 5 ppm.

This material powder mixture was then molded by utilizing a die-press molding machine thereby to form a molded body having a molding density of 9.3 g/cm$^3$ (relative density of 47.16%).

Next, thus obtained molded body was subjected to a calcining treatment by using a continuous hydrogen furnace under the conditions that a treating temperature was 1350° C., a feeding speed of the molded body was 4.5 to 5.0 cm/min. Then, thus obtained calcined body was subjected to a current-carrying sintering treatment (electrically heating and sintering treatment) in a bell jar through which hydrogen gas was flowing, under conditions that a sintering current was 3950 A and a sintering time was 75 min, thereby to obtain a rhenium tungsten ingot having a density of 19.1 g/cm$^3$ (relative density of 96.86%).

With respect to this rhenium tungsten ingot, a swaging work was conducted at a temperature of 1400° C. thereby to form a rod member having a diameter of 12.0 mm. Thereafter, the rod member was subjected to a current-carrying anneal treatment in a hydrogen gas atmosphere under the conditions that a current was 2900 A and a current-carrying time was 2 min. Further, after completion of a rolling work at a temperature of 1400° C., the swaging work was repeated at a temperature of 1400° C. thereby to form a rhenium tungsten rod member having a diameter of 6.0 mm.

With respect to this rhenium tungsten rod member, a recrystallizing treatment was conducted by heating the rod member to a temperature of 2400° C. using a high-frequency induction heating apparatus, thereby to obtain a rhenium tungsten rod member of which crystal grain size is within a range of 20 to 50 μm.

With respect to this rhenium tungsten rod member subjected to the recrystallizing treatment, a swaging work (step) was conducted at a temperature of 1400° C. under a condition that a reduction rate per one-pass was set to 12 to 18% thereby to obtain a rhenium tungsten rod member having a diameter of 2.2 mm.

With respect to this rhenium tungsten rod member, several times of drawing works were conducted at a temperature of 800 to 900° C. until a total reduction rate became to be 98.7% thereby to obtain a rhenium tungsten wire having a diameter of 0.22 mm.

In this regard, in the above drawing work, at a stage where the total reduction rate is 0% or more and less than 86% with respect to a cross sectional area at a time of starting the drawing work, a reduction rate per one-pass of the drawing work was controlled to be 28% to 37%. Further, at a stage of the total reduction rate was 86% or more and less than 97%, the reduction rate per one-pass of the drawing work is controlled to be 20% to 30%. Furthermore, at a stage of the total reduction rate of 97% or more, the reduction rate per one-pass of the drawing work was controlled to be 17% to 25%.

Next, with respect to thus obtained rhenium tungsten wire, a strainer work was conducted. Thereafter, an electrolytic polishing treatment was performed to a surface of the wire in an aqueous solution of sodium hydrate with a concentration of 7 to 15 mass %, so that a lubricant agent adhered to the surface of the wire and an oxide layer formed to the surface of the wire were removed thereby to obtain a rhenium tungsten wire having a diameter of 0.2 mm.

The rhenium tungsten wire after completion of the above electrolytic polishing work had been confirmed to have a tensile strength of 3510 N/mm$^2$ that was about 1.28 times higher than that of conventional wire member.

The tensile strength of the rhenium tungsten wire according to Example 1 belongs to a region (A) of Examples shown in FIG. 1 which is a graph showing a relation between the wire diameter D and the tensile strength T of various rhenium tungsten wires.

Further, with respect to thus obtained rhenium tungsten wire subjected to the electrolytic polishing treatment, a bending test shown in FIG. 2 was conducted. As a result, bending times until a crack was generated were as follows. Namely, an average bending times was 15.4, a minimum bending times was 13, and maximum bending times was 19, so that the respective rhenium tungsten wires exhibited a good bending property (durability).

Next, in order to evaluate characteristics of a medical needle according to the present invention, the rhenium tungsten wires prepared in the present Example were used, and the rhenium tungsten wires were subjected to strainer work, cutting work, and edging work using a mechanical grinding (polishing) thereby to manufacture needles each having a straight shape.

The strainer work was performed by using a rotary type strainer working machine, and a height of a chord per 100 mm-length of the rhenium tungsten wire was set to within a range of 10 mm or less in accordance with a circular-arc/chord method. The cutting work was conducted by using a grinding-stone cutter so as to provide a length of 50 mm. The mechanical grinding (polishing) work was performed in such a manner that a top end portion of a pin (needle) was abutted against a rotary grinding stone at an angle of 45°, so that the top end portion was worked to provide a tapered-shape and having an opening angle of 45°.

Thereafter, an upper portion having a 10 mm-length of thus manufactured needle was clamped and fixed to an apparatus. In this state, a block of pork (pig meat) was stabbed by using the needle into a depth of 30 mm for 50 times. After completion of the stabbing operation for 50 times, a bended amount (amount of deflection in bending) of the needle was measured. This bended amount of the needle was measured as a maximum displacement amount of the needle.

The above stabbing test was conducted to each of the respective 10 pieces of the needles. As a result, an average bended amount at a portion ranging from the top end portion to a potion 40 mm apart from the top end portion of the needle was 1.8 mm.

EXAMPLE 2

The same manufacturing processes as in Example 1 were repeated except that a mixing ratio of the rhenium powder was set to 10 parts by weight thereby to manufacture a rhenium tungsten wire having a wire diameter D of 0.2 mm according to Example 2.

With respect to thus obtained rhenium tungsten wire, the same evaluation as in Example 1 was performed. The evaluation results are shown in Table 1. As a result, it was confirmed that the rhenium tungsten wire of Example 2 had a tensile strength T fallen within a region (A) shown in FIG. 1 and had the tensile strength higher than those of conventional wire members, so that the crack formation was reduced.

EXAMPLE 3

The same manufacturing processes as in Example 1 were repeated except that the mixing ratio of the rhenium powder was set to 30 parts by weight thereby to manufacture a rhenium tungsten wire having a wire diameter D of 0.2 mm according to Example 3.

With respect to thus obtained rhenium tungsten wire, the same evaluation as in Example 1 was performed. The evaluation results are shown in Table 1. As a result, it was confirmed that the rhenium tungsten wire of Example 3 had a tensile strength higher than those of conventional wire members, so that the crack formation was reduced.

EXAMPLE 4

The same manufacturing processes as in Example 1 were repeated except that the rhenium powder having an average grain size D50 of 50 μm was used thereby to manufacture a rhenium tungsten wire having a wire diameter D of 0.2 mm according to Example 4.

With respect to thus obtained rhenium tungsten wire, the same evaluation as in Example 1 was performed. The evaluation results are shown in Table 1. The rhenium tungsten wire manufactured by Example 4 had a good tensile strength. However, a wire breaking was locally generated, so that a poor workability was posed as a problem.

EXAMPLE 5

The same manufacturing processes as in Example 1 were repeated except that the tungsten powder containing a total impurity amount of 500 ppm or more was used thereby to manufacture a rhenium tungsten wire having a wire diameter D of 0.2 mm according to Example 5.

With respect to thus obtained rhenium tungsten wire, the same evaluation as in Example 1 was performed. The evaluation results are shown in Table 1. The rhenium tungsten wire manufactured by Example 5 had a tensile strength fallen within a preferable region (A) shown in FIG. 1. However, there was caused a scattering (dispersion) in data values of the tensile strength.

EXAMPLE 6

The same manufacturing processes as in Example 1 were repeated except that the diameter of the rhenium tungsten rod member to be subjected to the high-frequency annealing treatment was set to 7.0 thereby to manufacture a rhenium tungsten wire having a wire diameter D of 0.1 mm according to Example 6.

With respect to thus obtained rhenium tungsten wire, the same evaluation as in Example 1 was performed. The evaluation results are shown in Table 1. As a result, it was confirmed that the rhenium tungsten wire manufactured by Example 6 had a tensile strength fallen within the region (A) shown in FIG. 1, and had the tensile strength higher than those of conventional wire members, so that the crack formation was reduced.

EXAMPLE 7

The same manufacturing processes as in Example 1 were repeated except that the diameter of the rhenium tungsten rod member to be subjected to the high-frequency annealing treatment was set to 5.1 mm thereby to manufacture a rhenium tungsten wire having a wire diameter D of 0.1 mm according to Example 7.

With respect to thus obtained rhenium tungsten wire, the same evaluation as in Example 1 was performed. The evaluation results are shown in Table 1. As a result, it was confirmed that the rhenium tungsten wire manufactured by Example 7 had a tensile strength fallen within the region (A) shown in FIG. 1, and had the tensile strength higher than those of conventional wire members, so that the crack formation could be reduced.

EXAMPLE 8

The same manufacturing processes as in Example 1 were repeated except that the diameter of the rhenium tungsten rod member to be subjected to the high-frequency annealing treatment was set to 7.0 mm thereby to manufacture a rhenium tungsten wire having a wire diameter D of 0.4 mm according to Example 8.

With respect to thus obtained rhenium tungsten wire, the same evaluation as in Example 1 was performed. The evaluation results are shown in Table 1. As a result, it was confirmed that the rhenium tungsten wire manufactured by Example 8 had a tensile strength fallen within the region (A) shown in FIG. 1, and had the tensile strength higher than those of conventional wire members, so that the crack formation could be reduced.

EXAMPLE 9

The same manufacturing processes as in Example 1 were repeated except that the diameter of the rhenium tungsten rod member to be subjected to the high-frequency annealing treatment was set to 5.1 mm, thereby to manufacture a rhenium tungsten wire having a wire diameter D of 0.4 mm according to Example 9.

With respect to thus obtained rhenium tungsten wire, the same evaluation as in Example 1 was performed. The evaluation results are shown in Table 1. As a result, it was confirmed that the rhenium tungsten wire manufactured by Example 9 had a tensile strength fallen within the region (A) shown in FIG. 1, and had the tensile strength higher than those of conventional wire members, so that the crack formation could be reduced.

EXAMPLE 10

The same manufacturing processes as in Example 1 were repeated except that the high-frequency annealing treatment was conducted at a temperature of 2300° C. thereby to manufacture a rhenium tungsten wire having a wire diameter D of 0.2 mm according to Example 10.

With respect to thus obtained rhenium tungsten wire, the same evaluation as in Example 1 was performed. The evaluation results are shown in Table 1. As a result, it was confirmed that the rhenium tungsten wire manufactured by Example 10 had a tensile strength fallen within the region (A) shown in FIG. 1, and had the tensile strength higher than those of conventional wire members, so that the crack formation could be reduced.

EXAMPLE 11

The same manufacturing processes as in Example 1 were repeated except that the high-frequency annealing treatment was conducted at a temperature of 2600° C. thereby to manufacture a rhenium tungsten wire having a wire diameter D of 0.2 mm according to Example 11.

With respect to thus obtained rhenium tungsten wire, the same evaluation as in Example 1 was performed. The evaluation results are shown in Table 1. As a result, it was confirmed that the rhenium tungsten wire manufactured by Example 11 had a tensile strength fallen within the region (A) shown in FIG. 1, and had the tensile strength higher than those of conventional wire members, so that the crack formation could be reduced.

COMPARATIVE EXAMPLE 1

The same manufacturing processes as in Example 1 were repeated except that the mixing ratio of the rhenium powder was set to an excessively small amount of 3 parts by weight thereby to manufacture a rhenium tungsten wire having a wire diameter D of 0.2 mm according to Comparative Example 1.

With respect to thus obtained rhenium tungsten wire, the same evaluation as in Example 1 was performed. The evaluation results are shown in Table 1.

The rhenium tungsten wire according to this Comparative Example 1 had been confirmed to have a tensile strength of 3070 N/mm$^2$. This tensile strength of the rhenium tungsten wire belongs to a region (B) of Conventional Examples shown in FIG. 1 which is a graph showing a relation between the wire diameter D and the tensile strength T of various rhenium tungsten wires.

COMPARATIVE EXAMPLE 2

The same manufacturing processes as in Example 1 were repeated except that the mixing ratio of the rhenium powder was set to an excessively large amount of 35 parts by weight thereby to manufacture a rhenium tungsten wire having a wire diameter D of 0.2 mm according to Comparative Example 2.

With respect to thus obtained rhenium tungsten wire, the same evaluation as in Example 1 was performed. The evaluation results are shown in Table 1.

In the rhenium tungsten wire according to this Comparative Example 2, an abnormal structure was formed thereby to cause breakage of the wire, so that it became impossible to further perform subsequent works for the wire.

COMPARATIVE EXAMPLE 3

74 parts by weight of tungsten powder having an average grain size D50 of 30 μm and an average grain size D90 of 50 μm was mixed with 26 parts by weight of rhenium powder having the average grain size D50 of 20 μm by means of a ball mill thereby to prepare a material powder mixture. Impurity contents of the tungsten powder are as follows. Namely, a content of Fe was less than 50 ppm, Mo was less than 20 ppm, O was less than 0.1 wt %, and K was less than 5 ppm.

This material powder mixture was then molded by utilizing a die-press molding machine thereby to form a molded body having a molding density of 9.3 g/cm$^3$.

Next, thus obtained molded body was subjected to a calcining treatment by using a continuous hydrogen furnace under the conditions that the treating temperature was 1350° C., the feeding speed of the molded body was 4.5 to 5.0 cm/min. Then, thus obtained calcined body was subjected to a current-carrying sintering treatment (electrically heating and sintering treatment) in a bell jar through which hydrogen gas was flowing, under conditions that a sintering current was 3650 A and sintering time was 50 min, thereby to obtain a rhenium tungsten ingot having a density of 19.1 g/cm$^3$.

With respect to this rhenium tungsten ingot, a swaging work was conducted at a temperature of 1400° C. thereby to form a rod member having a diameter of 12.0 mm. Thereafter, the rod member was subjected to a current-carrying anneal treatment in a hydrogen gas atmosphere under the conditions that the current was 2900 A and a current-carrying time was 2 min. Further, after completion of a rolling work at a temperature of 1400° C., the swaging work was repeated at a temperature of 1400° C. thereby to form a rhenium tungsten rod member having a diameter of 4.0 mm.

With respect to this rhenium tungsten rod member, a recrystallizing treatment was conducted by heating the rod member to a temperature of 2600° C. using the high-frequency induction heating apparatus, thereby to obtain a rhenium tungsten rod member of which crystal grain size is within a range of 40 to 80 μm.

With respect to this rhenium tungsten rod member subjected to the recrystallizing treatment, the same working processes (steps) as in Example 1 were conducted thereby to obtain a rhenium tungsten wire having a diameter of 0.2 mm. With respect to thus obtained rhenium tungsten wire, the same evaluation as in Example 1 was performed.

The tensile strength of the rhenium tungsten wire according to this Comparative Example 3 was 2740 N/mm$^2$. This value of the tensile strength of the rhenium tungsten wire belongs to a region (B) of Conventional Examples shown in FIG. 1 which is a graph showing a relation between the wire diameter D and the tensile strength T of various rhenium tungsten wires.

This rhenium tungsten wire was subjected to the bending test shown in FIG. 2 was conducted. As a result, bending times until a crack was generated were as follows. Namely, an average bending times was 10.4, a minimum bending times was 7, and a maximum bending times was 13. Further, in a bending test (stabbing test) where the rhenium tungsten wire was formed in a shape of needle, an average value of the bending amount was 5.7 mm. The evaluation results are shown in Table 1.

COMPARATIVE EXAMPLE 4

The same manufacturing processes as in Example 1 were repeated except that the diameter of the rhenium tungsten rod member to be subjected to the high-frequency annealing treatment was set to 4.0 thereby to manufacture a rhenium tungsten wire having a wire diameter D of 0.1 mm according to Comparative Example 4. With respect to thus obtained rhenium tungsten wire, the same evaluation as in Example 1 was performed. The evaluation results are shown in Table 1.

COMPARATIVE EXAMPLE 5

The same manufacturing processes as in Example 1 were repeated except that the diameter of the rhenium tungsten rod member to be subjected to the high-frequency annealing treatment was set to 4.0 thereby to manufacture a rhenium tungsten wire having a wire diameter D of 0.4 mm according to Comparative Example 5. With respect to thus obtained rhenium tungsten wire, the same evaluation as in Example 1 was performed. The evaluation results are shown in Table 1.

COMPARATIVE EXAMPLE 6

The same manufacturing processes as in Example 1 were repeated except that the high-frequency annealing treatment was conducted at a temperature of 2700° C. thereby to manufacture a rhenium tungsten wire having a wire diameter D of 0.2 mm according to Comparative Example 6. With respect to thus obtained rhenium tungsten wire, the same evaluation as in Example 1 was performed. The evaluation results are shown in Table 1.

COMPARATIVE EXAMPLE 7

The same manufacturing processes as in Example 1 were conducted thereby to manufacture a rhenium tungsten wire having a wire diameter D of 0.05 mm according to Comparative Example 7. With respect to thus obtained rhenium tungsten wire, the same evaluation as in Example 1 was performed. The evaluation results are shown in Table 1.

COMPARATIVE EXAMPLE 8

The same manufacturing processes as in Example 1 were conducted thereby to manufacture a rhenium tungsten wire having a wire diameter D of 0.45 mm according to Comparative Example 8. With respect to thus obtained rhenium tungsten wire, the same evaluation as in Example 1 was performed. The evaluation results are shown in Table 1.

The tensile strengths T with respect to each of the wire diameters D of the rhenium tungsten wires according to Examples 1 to 11 as explained above could be confirmed to exist in the region (A) shown in a graph indicated by FIG. 1.

On the other hand, it could be also confirmed that the tensile strengths T with respect to each of the wire diameters D of the rhenium tungsten wires according to Comparative Examples 1, 3 to 5 and 8 existed in the region (B) indicating Conventional Examples in a graph indicated by FIG. 1.

The manufacturing conditions and characteristics of the rhenium tungsten wires according to the above Examples and Comparative Examples are collectively shown in Table 1 hereunder.

TABLE 1

| Sample No. | Wire Diameter D (mm) | Grain Size D50 of Tungsten Powder (μm) | Grain Size D90 of Tungsten Powder (μm) | Grain Size D50 of Renium Powder (μm) | Addition Amount of Re (mass %) | Temperature for High Frequency Annealing (° C.) | Crystal Grain Size (μm) | High-Frequency Anneal conducting Diameter (mm) | Total Reduction Rate from High-Frequency Annealling Size (%) |
|---|---|---|---|---|---|---|---|---|---|
| Example 1 | 0.2 | 20 | 50 | 20 | 26 | 2400 | 20~50 | 6.0 | 99.889% |
| Example 2 | 0.2 | 20 | 50 | 20 | 10 | 2400 | 20~50 | 6.0 | 99.889% |
| Example 3 | 0.2 | 20 | 50 | 20 | 30 | 2400 | 20~50 | 6.0 | 99.889% |
| Example 4 | 0.2 | 20 | 50 | 50 | 26 | 2400 | 20~50 | 6.0 | 99.889% |
| Example 5 | 0.2 | 20 | 50 | 20 | 26 | 2400 | 20~50 | 6.0 | 99.889% |
| Example 6 | 0.1 | 20 | 50 | 20 | 26 | 2400 | 20~40 | 7.0 | 99.980% |
| Example 7 | 0.1 | 20 | 50 | 20 | 26 | 2400 | 30~50 | 5.1 | 99.962% |
| Example 8 | 0.4 | 20 | 50 | 20 | 26 | 2400 | 20~50 | 7.0 | 99.673% |
| Example 9 | 0.4 | 20 | 50 | 20 | 26 | 2400 | 30~50 | 5.1 | 99.385% |
| Example 10 | 0.2 | 20 | 50 | 20 | 26 | 2300 | 20~50 | 6.0 | 99.889% |
| Example 11 | 0.2 | 20 | 50 | 20 | 26 | 2500 | 20~50 | 6.0 | 99.889% |
| C. Example 1 | 0.2 | 20 | 50 | 20 | 3 | 2400 | 20~50 | 6.0 | 99.889% |
| C. Example 2 | 0.2 | 20 | 50 | 20 | 35 | 2400 | 20~50 | 6.0 | 99.889% |
| C. Example 3 | 0.2 | 30 | 50 | 20 | 26 | 2500 | 40~80 | 4.0 | 99.750% |
| C. Example 4 | 0.1 | 20 | 50 | 20 | 26 | 2400 | 40~80 | 4.0 | 99.938% |
| C. Example 5 | 0.4 | 20 | 50 | 20 | 26 | 2400 | 40~80 | 4.0 | 99.000% |
| C. Example 6 | 0.2 | 20 | 50 | 20 | 26 | 2700 | 20~50 | 6.0 | 99.889% |
| C. Example 7 | 0.05 | 20 | 50 | 20 | 26 | 2400 | 20~50 | 6.0 | 99.993% |
| C. Example 8 | 0.45 | 20 | 50 | 20 | 25 | 2400 | 20~50 | 6.0 | 99.438% |

| Sample No. | Tensile Strength T (N/mm$^2$) | Tensile Strength Region shown in FIG. 1 | Bending Times in Bending Test Average | Bending Times in Bending Test Minimum | Stabbing Test Average Bended Amount (mm) | Strength | Crack | Workability | Remarks |
|---|---|---|---|---|---|---|---|---|---|
| Example 1 | 3510 | A | 17.4 | 13 | 1.8 | ○ | ○ | ○ | Good |
| Example 2 | 3280 | A | 14.6 | 9 | 2.5 | ○ | ○ | ○ | Good |
| Example 3 | 3870 | A | 19.2 | 15 | 1.3 | ○ | ○ | ○ | Good |
| Example 4 | 3500 | A | 16.3 | 12 | 3.8 | ○ | ○ | Δ | Locally generated Breakage |

TABLE 1-continued

| | | | | | | | | | |
|---|---|---|---|---|---|---|---|---|---|
| Example 5 | 3470 | A | 16.5 | 10 | 3.5 | Δ | ○ | ○ | Largely Scattered in Tensile Strength |
| Example 6 | 4390 | A | 25.3 | 19 | 2.8 | ○ | ○ | ○ | Good |
| Example 7 | 3940 | A | 22.7 | 16 | 3.6 | ○ | ○ | ○ | Good |
| Example 8 | 2980 | A | 14.3 | 11 | 0.8 | ○ | ○ | ○ | Good |
| Example 9 | 2520 | A | 12.1 | 3 | 1.1 | ○ | ○ | ○ | Good |
| Example 10 | 3590 | A | 17.7 | 14 | 1.5 | ○ | ○ | ○ | Good |
| Example 11 | 3300 | A | 15.7 | 11 | 2.1 | ○ | ○ | ○ | Good |
| C. Example 1 | 3070 | B | 10.8 | 7 | 4.6 | x | Δ | Δ | Insufficient Strength |
| C. Example 2 | — | — | — | — | — | — | — | — | Not-workable due to Breakage caused by Abnormal Structure Formation |
| C. Example 3 | 2740 | B | 12.4 | 8 | 5.7 | Δ | ○ | x | Defects/Breakage/ Scattered in Tensile Strength |
| C. Example 4 | 3010 | B | 14.7 | 11 | 5.5 | x | ○ | ○ | Insufficient Strength |
| C. Example 5 | 1990 | B | 9.2 | 6 | 2.3 | x | ○ | ○ | Insufficient Strength |
| C. Example 6 | — | — | — | — | — | — | — | x | Not-workable due to Unstable Wire Diameter |
| C. Example 7 | — | — | — | — | — | — | — | x | Impossible to Draw due to Breakage of Wire |
| C. Example 8 | 2480 | — | 8.6 | 6 | 1.1 | x | | | |

C. Example denotes Comparative Example

As is clear from the results as explained above, it becomes clear that the rhenium tungsten wire having a tensile strength higher than those of conventional wire members can be obtained when the manufacturing process is adopted so as to optimize a grain size distribution of the material powders and to control the crystal grain size to an adequate range. In addition, it is also confirmed that this rhenium tungsten wire can greatly reduce cracks to be caused by bending the wire, so that this rhenium tungsten wire can be suitably used as a needle for medical use.

INDUSTRIAL APPLICABILITY

The present invention can provide a rhenium tungsten wire having a high tensile strength even if the wire diameter is made to be fine, and the rhenium tungsten wire hardly cause breaking or crack due to a bending operation for the wire, so that the rhenium tungsten wire can be suitably utilized as a medical needle.

The invention claimed is:

1. A rhenium tungsten wire, comprising:

tungsten; and 10-30 mass % of rhenium, having a wire diameter D of 0.10-0.40 mm, wherein a crystal grain size of the rhenium tungsten wire is 10 to 50 μm and a tensile strength T (N/mm$^2$) of the rhenium tungsten wire is within a range specified by equation (1)

$$6314.6\times D^2-7869.3\times D+4516.3\leq T\leq 5047.4\times D^2-7206.4\times D+5129.2 \quad (1).$$

2. The wire of claim 1, wherein a total content of Fe, Mo, Si, Mg, Al, and Ca is 200 ppm or less.

3. The wire of claim 2, comprising 24 to 27 mass % of rhenium.

4. The wire of claim 1, comprising 24 to 27 mass % of rhenium.

5. The wire of claim 1, in the form of a member comprised in a medical needle.

6. The wire of claim 2, in the form of a member comprised in a medical needle.

7. The wire of claim 1, wherein the tensile strength T (N/mm$^2$) of the rhenium tungsten wire is within a range specified by the following equation:

$$6314.6\times D^2-7869.3\times D+4516.3\leq T\leq 5047.4\times D^2-7206.4\times D+5129.2.$$

8. A rhenium tungsten wire, consisting essentially of:

tungsten; and 10-30 mass % of rhenium, having a wire diameter D of 0.10-0.40 mm, wherein a crystal grain size of the rhenium tungsten wire is 10 to 50 μm and a tensile strength T (N/mm$^2$) of the rhenium tungsten wire is within a range specified by equation (1)

$$6314.6\times D^2-7869.3\times D+4516.3\leq T\leq 5047.4\times D^2-7206.4\times D+5129.2 \quad (1).$$

9. The wire of claim 8, wherein a total content of Fe, Mo, Si, Mg, Al, and Ca is 200 ppm or less.

10. The wire of claim 9, comprising 24 to 27 mass % of rhenium.

11. The wire of claim 8, in the form of a member comprised in a medical needle.

12. The wire of claim 8, comprising 24 to 27 mass % of rhenium.

13. The wire of claim 8,wherein the tensile strength T (N/mm$^2$)of the rhenium tungsten wire is within a range specified by the following equation:

$$6314.6\times D^2-7869.3\times D+4516.3\leq T\leq 5047.4\times D^2-7206.4\times D+5129.2 \quad (1).$$

* * * * *